United States Patent

Fänger et al.

[11] Patent Number: 6,153,204
[45] Date of Patent: Nov. 28, 2000

[54] COSMETIC OR PHARMACEUTICAL PREPARATIONS WITH A REDUCED FEELING OF STICKINESS

[75] Inventors: Sabine Fänger, Hamburg; Stephanie von der Fecht, Schenefeld, both of Germany; Gertrudis Haest, Leuven, Belgium; Günther Schneider, Hamburg, Germany

[73] Assignees: Beirsdorf AG, Hamburg, Germany; Cerestar Holding B.V., La Sas Van Gent, Netherlands

[21] Appl. No.: 09/180,427

[22] PCT Filed: Apr. 24, 1997

[86] PCT No.: PCT/EP97/02091

§ 371 Date: Nov. 6, 1998

§ 102(e) Date: Nov. 6, 1998

[87] PCT Pub. No.: WO97/44009

PCT Pub. Date: Nov. 27, 1997

[30] Foreign Application Priority Data

May 17, 1996 [DE] Germany .............................. 196 19 837

[51] Int. Cl.$^7$ ................ A61K 7/00; A61K 7/44; A61K 7/025; A61K 7/38; A61K 7/035
[52] U.S. Cl. ............... 424/401; 424/60; 424/64; 424/68; 424/69; 514/938; 514/944
[58] Field of Search .................. 424/64, 65, 69, 424/401, 60, 68; 514/938, 944

[56] References Cited

U.S. PATENT DOCUMENTS 3,852,475  12/1974  Tarangul .
3,998,753  12/1976  Antoshkiw et al. .
4,981,677   1/1991  Thau .

FOREIGN PATENT DOCUMENTS 0 309 353   3/1989  European Pat. Off. .
0 583 756   2/1994  European Pat. Off. .
2 076 290  12/1981  United Kingdom .
95/06458    3/1995  WIPO .

OTHER PUBLICATIONS

Chemical Abstracts, vol. 124, No. 1 (1996), Abstract No. 7401, Trubiano, Paulo C.: The role of specialty food starches in flavor encapsulation and ACS Symp. Ser. (1995), 610 (Flavor Technology) 244–53: ACSMC8; ISSN: 0097–6156 (1995).

*Primary Examiner*—Diana Dudash
*Assistant Examiner*—Alysia Berman
*Attorney, Agent, or Firm*—Norris, McLaughlin & Marcus, P.A.

[57] ABSTRACT

Cosmetic or pharmaceutical preparations, characterized in that they comprise an effective concentration of hydrophilic starch esterified with one or more n-octenylsuccinate radicals.

8 Claims, No Drawings

COSMETIC OR PHARMACEUTICAL PREPARATIONS WITH A REDUCED FEELING OF STICKINESS

This application is a 371 of PCT/E97/02091 filed Apr. 24, 1997.

The present invention relates to cosmetic or pharmaceutical preparations with a reduced feeling of stickiness, to a process for their preparation and to the use of active ingredients for reducing the feeling of stickiness of cosmetic preparations.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes).

If this function becomes impaired, increased resorption of toxic or allergenic substances or infection by microorganisms may result, leading to toxic or allergic skin reactions.

Another aim of skin care is to compensate for the loss by the skin of grease and water caused by daily washing. This is particularly important if the natural regeneration ability is inadequate. Furthermore, skin-care products should protect against environmental influences, in particular against sun and wind, and delay skin ageing.

Medicinal compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Regulation, Foods and Drugs Act).

Cosmetic or dermatological preparations are frequently in the form of finely dispersed multiphase systems in which one or more fatty or oily phases are present alongside one or more aqueous phases. Of these systems, the actual emulsions are, in turn, the most widespread.

In simple emulsions, one phase contains finely disperse droplets of the second phase, surrounded by an emulsifier shell (water droplets in W/O emulsions or lipid vesicles in O/W emulsions). In a multiple emulsion (second degree), on the other hand, such droplets contain finely disperse droplets of the first phase in emulsified form. These droplets may in turn contain even more finely disperse droplets (third degree multiple emulsion) and so on.

Thus, just as reference is made in the case of simple emulsions to W/O or O/W emulsions (Water-in-Oil or Oil-in-Water), in the case of multiple emulsions reference is made to W/O/W, O/W/O, O/W/O/W, W/O/W/O emulsions and so on.

The droplet diameters of customary emulsions are in the range from approximately 1 $\mu$m to approximately 50 $\mu$m. Such "macroemulsions" are, without other colouring additives, milky white in colour and opaque. Finer "macroemulsions", whose droplet diameters are in the range from approximately $10^{-1}$ $\mu$m to approximately 1 $\mu$m, are, again without colouring additives, blueish white in colour and opaque.

Only micellar and molecular solutions having particle diameters of less than approximately $10^{-2}$ $\mu$m appear clear and transparent.

The droplet diameter of transparent or translucent microemulsions, on the other hand, is in the range from about $10^{-2}$ $\mu$m to about $10^{-1}$ $\mu$m. Such microemulsions usually have a low viscosity. The viscosity of many microemulsions of the O/W type is comparable with that of water.

An advantage of microemulsions is that the disperse phase can contain active ingredients in more finely disperse form than in the disperse phase of "macroemulsions". A further advantage is that, because of their low viscosity, they can be sprayed. If microemulsions are used as cosmetics, the corresponding products are distinguished by high cosmetic elegance.

The use of customary cosmetic emulsifiers is in itself acceptable. Nevertheless, emulsifiers, like ultimately any chemical substance, may in certain circumstances cause allergic reactions or reactions based on over-sensitivity of the user.

For example, it is known that certain light dermatoses are triggered by certain emulsifiers, but also by a variety of fats, and simultaneous exposure to sunlight. Such light dermatoses are also called "Mallorca acne".

Emulsifier-free cosmetic preparations, often in the form of light protection preparations, based on hydrodispersions have been available to the consumer for some time.

Hydrodispersions are dispersions of a liquid, semi-solid or solid internal (discontinuous) lipid phase in an external aqueous (continuous) phase.

However, in contrast to O/W emulsions, which are distinguished by a similar phase arrangement, hydrodispersions are essentially free from emulsifiers. Hydrodispersions are metastable systems, as furthermore are emulsions, and tend to pass into a state of two coherent discrete phases. In emulsions, the choice of a suitable emulsifier prevents phase separation.

In the case of hydrodispersions of a liquid lipid phase in an external aqueous phase, the stability of such a system can be ensured, for example, by building up a gel structure in the aqueous phase, in which structure the lipid droplets are suspended in a stable form.

W/O lipodispersions, which are the subject-matter of the present invention, are, by reverse analogy, emulsifier-free finely disperse preparations of the water-in-oil type.

Customary cosmetic and dermatological preparation forms, which have become more and more widespread particularly in recent times, which are emulsifier-free but which can also contain emulsifier, are gels. In the technical sense, gels are taken to mean: relatively dimensionally stable, easily deformable disperse systems of at least two components, which as a rule comprise a—usually solid—colloidally divided substance of long-chain molecular groupings (e.g. gelatin, silica, polysaccharides) as the skeleton-former and a liquid dispersant (e.g. water). The colloidally divided substance is often referred to as a thickener or gelling agent. It forms a spatial network in the dispersant, it being possible for individual particles present in colloidal form to be linked to one another to a greater or lesser degree via electrostatic interaction. The dispersant, which surrounds the network, is distinguished by electrostatic affinity for the gelling agent, i.e. a predominantly polar (in particular: hydrophilic) gelling agent preferably gels a polar dispersant (in particular: water), whereas a predominantly nonpolar gelling agent preferably gels nonpolar dispersants.

Strong electrostatic interactions, which are realized, for example, in hydrogen bridge bonds between gelling agent and dispersant, but also between dispersant molecules with one another, can lead to a high degree of crosslinking of the dispersant as well. Hydrogels can comprise water to the extent of almost 100% (along-side, for example, about 0.2–1.0% of a gelling agent) and at the same time have an entirely solid consistency. The water content is present here in ice-like structural elements, so that gels entirely justify the origin of their name [from Latin "gelatum"="frozen" by the alchimistic term "gelatina" (16th century) for the modern term "gelatin"].

In cosmetic and pharmaceutical technology, furthermore, lipogels and oleogels (from waxes, fats and fatty oils) as well as carbogels (from paraffin or petrolatum) are commonplace. In practice, a distinction is made between oleogels, which are in practically anhydrous form, and hydrogels, which are practically fat-free. In most cases, gels are transparent. In cosmetic and pharmaceutical technology, gels are as a rule distinguished by a semi-solid, often free-flowing, consistency.

Cosmetic sticks, in particular lipsticks, preferably lipcare sticks, but also deodorant sticks ("deosticks") are also common preparations.

The skin of the lips has only a very thin horny layer. There are no sweat glands on the lips, only a few sebaceous glands. The skin of the lips is therefore virtually free from fat and is prone to drying out, particularly in cold and dry weather. Small cracks may form in the skin, and the sensitivity of the lips to chemical, physical and microbial effects (e.g. food, sunlight, Herpes simplex viruses) increases.

It is the purpose of lipcare sticks to prevent this from happening. These products usually contain a large amount of waxes and fatty components which form a covering layer on the lips after application.

From a technical point of view, virtually all lipsticks are water-free fatty mixtures composed of solid or semi-solid waxes and liquid oils, the ultra-pure paraffin oils and waxes being the lipstick base.

The ideal profile of requirements includes smooth application of the lipsticks, but also of other cosmetic stick formulations, e.g. deodorizing sticks (deosticks), without substantial friction resistance. In particular, a lipstick should give a non-greasy, dull or sticky fatty film on the lips, even when pressed on slightly, which should nevertheless adhere well. This fatty film is intended to make the lips smooth and soft.

A stylistic element of decorative cosmetics is to match the lip colour with the type of person using suitable cosmetics.

Products of this type are, for example, decorative lipsticks, into which a very wide range of colour pigments can be incorporated. These sticks contain large amounts of waxes and fatty components which form a covering lipid layer on the lips after application.

In particular, preparations for cosmetic or therapeutic skincare comprise, as essential constituents, mixtures of oils or oil-soluble substances and water or water-soluble substances. Certain constituents of the aqueous phase, e.g. glycerol, but also of the oil phase, e.g. tocopheryl acetate, have, in relatively high concentrations, a negative effect on the sensory properties of the preparations. This frequently results in an increased feeling of stickiness or also feeling of greasiness when the respective preparations are applied, which then may, in certain circumstances, be unmarketable since they are viewed in negative terms and not accepted by the consumer.

It is admittedly known that this feeling of stickiness or feeling of greasiness can be reduced by adding specific substances, for example certain selected powdered raw materials, in particular talc. Apart from the fact that this is only rarely completely successful, such an addition also changes the viscosity of the product concerned and reduces stability.

The object was thus to remedy all of these disadvantages of the prior art. In particular, the aim was to provide products having reduced stickiness and greasiness. Products in the field of care cosmetics, decorative cosmetics and pharmacological technology were likewise to be freed from the prior art disadvantages which have been described.

It was also an object of the invention to develop cosmetic bases for cosmetic preparations which are well tolerated by the skin.

Another object of the present invention was to provide products having as broad an application diversity as possible. For example, the aim was to provide bases for preparation forms such as cleansing emulsions, face-care and body-care preparations, but also to provide distinct medical-pharmaceutical application forms, for example preparations against acne and other skin conditions.

Surprisingly, all of these objects have been achieved by cosmetic or pharmaceutical preparations, characterized in that they comprise an effective concentration of hydrophilic starch esterified with one or more n-octenylsuccinate radicals.

The invention further relates to the use of hydrophilic starch esterified with one or more n-octenylsuccinate radicals for reducing the stickiness and/or greasiness of cosmetic or pharmaceutical preparations.

The starch derivatives used according to the invention are distinguished by a structure starch-$X_n$, where X symbolizes the radical

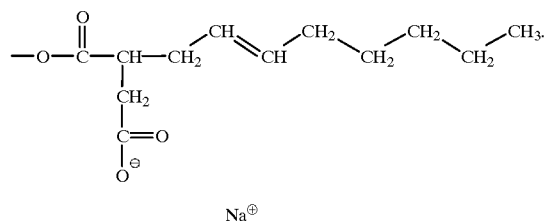

Starch derivatives which are advantageously to be used according to the invention do not yet have official INCI names (International Nomenclature of Cosmetic Ingredients); the name for these would have to be "starch sodium octenyl succinate". Those products which are marketed under the name Amiogum®, in particular Amiogum® 23 from Cerestar U.S., are particularly advantageous.

According to the invention, the content of starch derivatives used according to the invention (also referred to below as "active ingredient used according to the invention") in the cosmetic or topical dermatological preparations can be 0.01–25% by weight, preferably 0.1–10% by weight, in particular 0.2–5.0% by weight, based on the total weight of the preparations.

Surprisingly, it has been found that the active ingredient used according to the invention achieves the objects on which the invention is based.

The active ingredient used according to the invention can advantageously be incorporated into customary cosmetic and dermatological preparations, which can exist in various forms. They can, for example, be a solution, an emulsion of the water-in-oil (W/O) type or of the oil-in-water (O/W) type, or a multiple emulsion, for example of the water-in-oil-in-water (W/O/W) type or oil-in-water-in-oil (O/W/O) type, a hydrodispersion or lipodispersion, a gel, a solid stick or an aerosol.

For the purposes of the present invention, emulsions according to the invention, for example in the form of a skin protection cream, a skincare lotion, a cosmetic milk, for example in the form of a sun protection cream or a sun protection milk, are advantageous and contain, for example, fats, oils, waxes and/or other fatty substances, and water and one or more emulsifiers as are customarily used for this type of formulation.

For the purposes of the present invention, it is also possible and advantageous to add the active ingredient used according to the invention to aqueous systems or surfactant preparations for the cleansing of the skin and the hair.

The person skilled in the art is of course aware that demanding cosmetic compositions are in most cases inconceivable without the customary auxiliaries and additives. These include, for example, consistency regulators, fillers, perfume, dyes, emulsifiers, additional active ingredients such as vitamins or proteins, light protection agents, stabilizers, insect repellents, alcohol, water, salts, antimicrobial, proteolytic or keratolytic substances, etc.

Corresponding requirements apply mutatis mutandis to the formulation of medicinal preparations.

For the purposes of the present invention, medicinal topical compositions generally contain one or more medicaments in an effective concentration. For the sake of simplicity, in order to distinguish clearly between cosmetic and medicinal use and corresponding products, reference is made to the legal provisions in the Federal Republic of Germany (for example Cosmetics Regulation, Foods and Drugs Act).

It is also advantageous to add the active ingredient used according to the invention as additive to preparations which already contain other active ingredients for other purposes.

Accordingly, for the purposes of the present invention cosmetic or topical dermatological compositions can, depending on their composition, be used for example as skin protection cream, cleansing milk, sunscreen lotion, nourishing cream, day or night cream etc. If desired, it is possible and advantageous to use the compositions according to the invention as a base for pharmaceutical formulations.

In particular, the active ingredient used according to the invention can be used as an additive in cosmetic deodorants or antiperspirants. The deodorizing or antiperspirant agents used are the customary substances known to the person skilled in the art. For example, astringents—predominantly aluminium salts such as aluminium hydroxychloride (aluminium chlorohydrate)—can suppress the formation of perspiration.

The use of antimicrobial substances in cosmetic deodorants can reduce the bacterial flora on the skin. In this connection, in an ideal case, only the microorganisms causing the odour should be effectively reduced. Monocarboxylic esters of di- and triglycerol are, for example, advantageous. Other antimicrobial substances are, however, also suitable.

According to the invention, even the use of active ingredients which themselves do not have a particularly mild deodorizing or antiperspirant action is possible and, in some circumstances, advantageous since their possible erythema-promoting effect can be compensated by the active ingredient used according to the invention.

Those cosmetic and dermatological preparations which exist in the form of a sunscreen are also favourable. In addition to the active ingredient used according to the invention, these also preferably contain at least one UVA filter substance and/or at least one UVB filter substance and/or at least one inorganic pigment.

However, it is also advantageous for the purposes of the present invention to provide cosmetic and dermatological preparations whose main purpose is not protection against sunlight, but which nevertheless still contain anti-UV substances. Thus, for example, UV-A and UV-B filter substances are usually incorporated in day creams.

Preparations according to the invention can advantageously contain substances which absorb UV radiation in the UVB region, the total amount of filter substances being for example from 0.1% by weight to 30% by weight, preferably from 0.5 to 10% by weight, in particular from 1 to 6% by weight, based on the total weight of the preparations.

The UVB filters can be oil-soluble or water-soluble. Examples of oil-soluble substances which may be mentioned are:

3-benzylidenecamphor and derivatives thereof, e.g. 3-(4-methylbenzylidene)camphor, 4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

2,4,6-trianilino(p-carbo-2'-ethyl-1'-hexyloxy)-1,3,5-triazine

Advantageous water-soluble substances are:

2-phenylbenzimidazole-5-sulphonic acid and salts thereof, for example sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)sulphonic acid and its salts.

The list of given UVB filters which can be used according to the invention is of course not intended to be limiting.

The invention also provides the combination of a UVA filter according to the invention with a UVB filter or a cosmetic or dermatological preparation according to the invention which also contains a UVB filter.

It can also be advantageous to use UVA filters which are usually present in cosmetic and/or dermatological preparations in the preparations according to the invention. Such filter substances are preferably derivatives of dibenzoylmethane, in particular 1-(4'-tert-butylphenyl)-3-(4'-methoxyphenyl)propane-1,3-dione and 1-phenyl-3-(4,-isopropylphenyl)propane-1,3-dione. Preparations which contain these combinations are also a subject-matter of the invention. The same amounts of UVA filter substances which were given for UVB filter substances can be used.

For the purposes of the present invention, cosmetic and/or dermatological preparations can also contain inorganic pigments which are usually used in cosmetics for protecting the skin against UV radiation. These are oxides of titanium, zinc, iron, zirconium, silicon, manganese, aluminium, cerium and mixtures thereof, and modifications in which the oxides are the active agents. Particular preference is given to pigments based on titanium dioxide. The quantities given for the above combinations can be used.

The cosmetic and dermatological preparations according to the invention can contain cosmetic active ingredients, auxiliaries and/or additives as are usually used in such preparations, for example antioxidants, preservatives, bactericides, perfumes, antifoams, dyes, pigments which have a colouring effect, thickeners, surfactants, emulsifiers, softeners, moisturizers and/or humectants, fats, oils, waxes or other usual constituents of a cosmetic or dermatological formulation, such as alcohols, polyols, polymers, foam stabilizers, electrolytes, organic solvents or silicone derivatives.

For the purposes of the present invention, it is advantageous to add other antiirritative or antiinflammatory active ingredients to the preparations, in particular batyl alcohol (α-octadecyl glyceryl ether), selachyl alcohol (α-9-octadecenyl glyceryl ether), chimyl alcohol (α-hexadecyl glyceryl ether), bisabolol and/or panthenol.

It is likewise advantageous to add conventional antioxidants to the preparations for the purposes of the present invention. According to the invention, favourable antioxidants used can be any antioxidants which are suitable or customary for cosmetic and/or dermatological applications.

The antioxidants are advantageously selected from the group consisting of amino acids (for example glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very small tolerated doses (e.g. pmol to $\mu$mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and coniferylbenzoate of benzoin, rutinic acid and derivatives thereof, ferulic acid and derivatives thereof, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant(s), it is advantageous to choose their respective concentrations from the range 0.001–10% by weight, based on the total weight of the formulation.

For the purposes of the present invention, if the cosmetic or dermatological preparation is a solution or emulsion or dispersion, the solvent used can be:

water or aqueous solutions oils, such as triglycerides of capric or caprylic acid, but preferably castor oil;

fats, waxes and other natural and synthetic fatty substances, preferably esters of fatty acids with alcohols of low carbon number, for example with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the aforementioned solvents are used. In the case of alcoholic solvents, water can be a further constituent.

The oil phase of the emulsions, oleogels or hydrodispersions or lipodispersions for the purposes of the present invention is advantageously selected from the group consisting of esters of saturated and/or unsaturated, branched and/or unbranched alkanecarboxylic acids having a chain length of from 3 to 30 carbon atoms, and saturated and/or unsaturated, branched and/or unbranched alcohols having a chain length of from 3 to 30 carbon atoms, from the group consisting of esters of aromatic carboxylic acids and saturated and/or unsaturated, branched and/or unbranched alcohols having a chain length of from 3 to 30 carbon atoms. Such ester oils can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, e.g. jojoba oil.

In addition, the oil phase can advantageously be selected from the group consisting of branched and unbranched hydrocarbons and waxes, silicone oils, dialkyl ethers, the group consisting of saturated or unsaturated, branched or unbranched alcohols, and fatty acid triglycerides, in particular the triglycerol esters of saturated and/or unsaturated, branched and/or unbranched alkanecarboxylic acids having a chain length of from 8 to 24, in particular 12 to 18 carbon atoms. The fatty acid triglycerides can for example be advantageously selected from the group consisting of synthetic, semi-synthetic and natural oils, e.g. olive oil, sunflower oil, soy oil, groundnut oil, rapeseed oil, almond oil, palm oil, coconut oil, palm kernel oil etc.

Any desired mixtures of such oil and wax components can also advantageously be used for the purposes of the present invention. If desired, it can also be advantageous to use waxes, for example cetyl palmitate, as the sole lipid component of the oil phase.

The oil phase is advantageously selected from the group consisting of 2-ethylhexyl isostearate, octyl dodecanol, isotridecyl isononanoate, isoeicosane, 2-ethylhexyl cocoate, $C_{12-15}$-alkyl benzoate, caprylic/capric triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Advantageous hydrocarbons used for the purposes of the present invention are paraffin oil, squalane and squalene.

In addition, the oil phase can advantageously contain cyclic or linear silicone oils or consist entirely of such oils, although it is preferred that an additional content of other oil phase components apart from the silicone oil or the silicone oils be used.

Cyclomethicone (octamethylcyclotetrasiloxane) is advantageously employed as the silicone oil to be used according to the invention. However, other silicone oils are also advantageous for the purposes of the present invention, for example hexamethylcyclotrisiloxane, polydimethylsiloxane, poly(methylphenylsiloxane).

In addition, mixtures of cyclomethicone and isotridecyl isononanoate and of cyclomethicone and 2-ethylhexyl isostearate are particularly advantageous.

Gels used according to the invention usually contain alcohols of low carbon number, e.g. ethanol, isopropanol, 1,2-propanediol, glycerol and water or an oil mentioned above in the presence of a thickener, which, for oily-alcoholic gels, is preferably silicon dioxide or an aluminium silicate and, for aqueous-alcoholic or alcoholic gels, is preferably a polyacrylate.

Solid sticks contain, for example, natural or synthetic waxes, fatty alcohols or fatty acid esters. Preference is given to lipcare sticks and stick formulations for body deodorization.

Usual base substances which are suitable for use as cosmetic sticks for the purposes of the present invention are liquid oils (e.g. paraffin oils, castor oil, isopropyl myristate), semi-solid constituents (e.g. Vaseline, lanolin), solid constituents (e.g. beeswax, ceresin and microcrystalline waxes and ozokerite) and high-melting waxes (e.g. carnauba wax, candelilla wax).

For the purposes of the present invention, suitable propellants for cosmetic and/or dermatological preparations which can be sprayed from aerosol containers are the customary known, readily volatile, liquefied propellants, for example hydrocarbons (propane, butane, isobutane), which can be used on their own or in mixtures with one another. The use of compressed air is also advantageous.

The person skilled in the art obviously knows that there are propellent gases which are non-toxic per se which would in principle be suitable for realizing the present invention in the form of aerosol preparations but which, because of their harmful effect on the environment or other accompanying circumstances, should nevertheless be avoided, in particular fluorinated hydrocarbons and chlorofluorocarbons (CFCs).

For the purposes of the present invention, if the cosmetic or dermatological preparations are in the form of a lotion which is rinsed out and is used, for example, before or after bleaching, before or after shampooing, between two shampoos or before or after permanent wave treatment, the preparations are, for example, aqueous or aqueous-alcoholic solutions, which comprise surface-active substances if appropriate, preferably nonionic or cationic surface-active substances, the concentration of which can be between 0.1 and 10% by weight, preferably between 0.2 and 5% by weight. These cosmetic and/or dermatological preparations can also be aerosols with the auxiliaries usually used for this purpose.

For the purposes of the present invention, a cosmetic preparation in the form of a lotion which is not rinsed out, in particular a lotion for setting the hair, a lotion which is used for blow-drying the hair, a styling and treatment lotion, is generally an aqueous, alcoholic or aqueous-alcoholic solution and comprises at least one cationic, anionic, non-ionic or amphoteric polymer, or else mixtures thereof, as well as the active ingredient combinations according to the invention. The amount of polymers used is, for example, between 0.1 and 10% by weight, preferably between 0.1 and 3% by weight.

For the purposes of the present invention, cosmetic preparations for the treatment and care of the hair which comprise the active ingredient used according to the invention can be in the form of emulsions which are of the nonionic or anionic type. Nonionic emulsions comprise, as well as water, oils or fatty alcohols, which can also be polyethoxylated or polypropoxylated, for example, or also mixtures of the two organic components. If appropriate, these emulsions comprise cationic surface-active substances.

For the purposes of the present invention, cosmetic preparations for the treatment and care of the hair can be in the form of gels which, in addition to an effective content of active ingredient according to the invention and solvents which are usually used therefor, preferably water, also contain organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminium silicates, such as, for example, bentonites, or a mixture of polyethylene glycol and polyethylene glycol stearate or distearate. The thickener is present in the gel e.g. in an amount of between 0.1 and 30% by weight, preferably between 0.5 and 15% by weight.

The following examples serve to illustrate the present invention.

EXAMPLE 1

W/O Emulsion

|  | % by weight |
|---|---|
| PEG-7 hydrogenated castor oil | 4.00 |
| Wool wax alcohol | 1.50 |
| Beeswax | 3.00 |
| Vaseline | 4.00 |
| Ozokerite | 4.00 |
| Paraffin oil, subliquidum | 10.00 |
| Glycerol | 15.00 |
| Octyl methoxycinnamate | 2.50 |
| Methylbenzylidenecamphor | 2.50 |
| Tocopherol acetate | 1.00 |
| Amiogum ® 23 (Starch Sodium Octenyl Succinate) | 0.50 |
| Magnesium sulphate 7H$_2$O | 0.70 |
| Perfume, preservative, dyes, antioxidants etc. | q.s. |
| Water | ad 100.00 |

EXAMPLE 2

W/O Emulsion

|  | % by weight |
|---|---|
| PEG-7 hydrogenated castor oil | 4.00 |
| Wool wax alcohol | 1.50 |
| Beeswax | 3.00 |
| Vaseline | 9.00 |
| Ozokerite | 4.00 |
| Paraffin oil, subliquidum | 10.00 |

-continued

| | % by weight |
|---|---|
| Sorbitol | 15.00 |
| Amiogum ® 23 (Starch Sodium Octenyl Succinate) | 0.50 |
| Magnesium sulphate 7H$_2$O | 0.70 |
| Perfume, preservative, dyes, antioxidants etc. | q.s. |
| Water | ad 100.00 |

EXAMPLE 3

W/O Emulsion

| | % by weight |
|---|---|
| PEG-7 hydrogenated castor oil | 4.00 |
| Wool wax alcohol | 1.50 |
| Beeswax | 3.00 |
| Vaseline | 9.00 |
| Ozokerite | 4.00 |
| Paraffin oil, subliquidum | 10.00 |
| Urea | 10.00 |
| Amiogum ® 23 (Starch Sodium Octenyl Succinate) | 0.50 |
| Magnesium sulphate 7H$_2$O | 0.70 |
| Lactic acid | 0.30 |
| Sodium lactate | 2.50 |
| Perfume, preservative, dyes, antioxidants etc. | q.s. |
| Water | ad 100.00 |

EXAMPLE 4

W/O Emulsion

| | % by weight |
|---|---|
| PEG-7 hydrogenated castor oil | 4.00 |
| Wool wax alcohol | 1.50 |
| Beeswax | 3.00 |
| Vaseline | 9.00 |
| Ozokerite | 4.00 |
| Paraffin oil, subliquidum | 10.00 |
| Glycerol | 15.00 |
| Tocopherol acetate | 1.00 |
| Amiogum ® 23 (Starch Sodium Octenyl Succinate) | 0.50 |
| Zinc sulphate 7H$_2$O | 0.70 |
| Glycine | 1.50 |
| Perfume, preservative, NaOH, dyes, antioxidants etc. | q.s. |
| Water | ad 100.00 |

EXAMPLE 5

W/O Emulsion

| | % by weight |
|---|---|
| Polyglyceryl-3 dioleate | 3.50 |
| Ozokerite | 3.00 |
| Beeswax | 2.00 |
| Paraffin oil, subliquidum | 10.00 |
| Cetearyl octanoate | 10.00 |
| Serine | 0.50 |
| Sorbitol | 9.00 |

-continued

| | % by weight |
|---|---|
| Glycerol | 9.00 |
| Amiogum ® 23 (Starch Sodium Octenyl Succinate) | 0.50 |
| Magnesium sulphate 7H$_2$O | 0.70 |
| Perfume, preservative, dyes, antioxidants etc. | q.s. |
| Water | ad 100.00 |

EXAMPLE 6

W/O Emulsion

| | % by weight |
|---|---|
| Laurylmethicone copolyol | 1.50 |
| Cetylmethicone copolyol | 0.50 |
| Paraffin oil, subliquidum | 10.00 |
| Cyclomethicone | 2.00 |
| Dimethicone | 1.00 |
| Wheatgerm oil | 4.00 |
| Capric/caprylic triglycerides | 4.00 |
| Glycerol | 10.00 |
| Amiogum ® 23 (Starch Sodium Octenyl Succinate) | 0.25 |
| Sodium chloride | 1.00 |
| Perfume, preservative, dyes, antioxidants etc. | q.s. |
| Water | ad 100.00 |

EXAMPLE 7

O/W Emulsion

| | % by weight |
|---|---|
| Sorbitan monostearate | 2.50 |
| Glyceryl monostearate | 1.00 |
| Vaseline | 0.50 |
| Paraffin oil, subliquidum | 11.00 |
| Octyldodecanol | 4.00 |
| Hydrogenated coconut fatty acid glycerides | 1.00 |
| Cyclomethicone | 1.00 |
| Carbomer | 0.15 |
| Glycerol | 10.00 |
| Tocopheryl acetate | 1.00 |
| Amiogum ® 23 (Starch Sodium Octenyl Succinate) | 0.50 |
| Perfume, preservative, NaOH, dyes, antioxidants etc. | q.s. |
| Water | ad 100.00 |

EXAMPLE 8

O/W Emulsion

| | % by weight |
|---|---|
| Stearic acid | 1.50 |
| Sorbitan monostearate | 0.50 |
| Myristyl alcohol | 1.50 |
| Glyceryl monostearate | 0.50 |
| Paraffin oil, subliquidum | 10.00 |
| Dimethicone | 1.00 |
| Octyldodecanol | 2.00 |
| Hydrogenated coconut fatty acid glycerides | 0.50 |

-continued

| | % by weight |
|---|---|
| Carbomer | 0.10 |
| Serine | 0.50 |
| Glycerol | 5.00 |
| Tocopheryl acetate | 0.50 |
| Amiogum ® 23 (Starch Sodium Octenyl Succinate) | 0.50 |
| Perfume, preservative, NaOH, dyes, antioxidants etc. | q.s. |
| Water | ad 100.00 |

EXAMPLE 9

O/W Emulsion

| | % by weight |
|---|---|
| Sorbitan monostearate | 2.00 |
| Laurylmethicone copolyol | 0.35 |
| Cetylmethicone copolyol | 0.15 |
| Paraffin oil, subliquidum | 10.00 |
| Octyldodecanol | 4.00 |
| Hydrogenated coconut fatty acid glycerides | 1.00 |
| Cyclomethicone | 1.00 |
| Dimethicone | 1.00 |
| Carbomer | 0.15 |
| Glycerol | 10.00 |
| Tocopheryl acetate | 1.00 |
| Amiogum ® 23 (Starch Sodium Octenyl Succinate) | 0.50 |
| Perfume, preservative, NaOH, dyes, antioxidants etc. | q.s. |
| Water | ad 100.00 |

EXAMPLE 10

O/W Emulsion

| | % by weight |
|---|---|
| Quaternium-5 | 3.50 |
| Paraffin oil, subliquidum | 10.00 |
| Cetearyl alcohol | 2.00 |
| Hydrogenated coconut fatty acid glycerides | 0.50 |
| Dimethicone | 0.75 |
| Glycerol | 20.00 |
| Tocopheryl acetate | 0.50 |
| Amiogum ® 23 (Starch Sodium Octenyl Succinate) | 0.50 |
| Perfume, preservative, NaOH, dyes, antioxidants etc. | q.s. |
| Water | ad 100.00 |

EXAMPLE 11

Hydrodispersion Gel

| | % by weight |
|---|---|
| PEG-8 (polyethylene glycol 400) | 5.00 |
| Ethanol | 2.00 |
| Carbomer | 0.70 |
| Triglyceride, liquid | 1.50 |
| Amiogum ® 23 (Starch Sodium Octenyl Succinate) | 1.25 |
| Glycerol | 5.00 |
| Sorbitol | 2.00 |

-continued

| | % by weight |
|---|---|
| Panthenol | 0.50 |
| Tocopheryl acetate | 0.50 |
| Perfume, preservative, NaOH, dyes, antioxidants etc. | q.s. |
| Water | ad 100.00 |

EXAMPLE 12

Hydrogel

| | % by weight |
|---|---|
| PEG-8 (polyethylene glycol 400) | 5.00 |
| Ethanol | 2.00 |
| Carbomer | 0.70 |
| Amiogum ® 23 (Starch Sodium Octenyl Succinate) | 1.25 |
| Glycerol | 5.00 |
| Sorbitol | 2.00 |
| Panthenol | 0.50 |
| Tocopheryl acetate | 0.50 |
| Perfume, preservative, NaOH, dyes, antioxidants etc. | q.s. |
| Water | ad 100.00 |

EXAMPLE 13

Lipcare Stick

| | % by weight |
|---|---|
| Caprylic/capric triglycerides | 27.00 |
| Octyldodecanol | 27.00 |
| Beeswax | 15.00 |
| Cetyl palmitate | 5.00 |
| Amiogum ® 23 (Starch Sodium Octenyl Succinate) | 0.25 |
| Squalane | 13.00 |
| Jojoba oil | 10.00 |
| Carnauba wax | 2.00 |
| Tocopheryl acetate | 0.75 |
| Perfume, preservative, antioxidants etc. | q.s. |

EXAMPLE 14

Emulsion Lipcare Stick

| | % by weight |
|---|---|
| Caprylic/capric triglycerides | 30.00 |
| Octyldodecanol | 20.00 |
| Polyglyceryl-3 dioleate | 3.50 |
| Beeswax | 12.50 |
| Amiogum ® 23 (Starch Sodium Octenyl Succinate) | 0.25 |
| Squalane | 11.00 |

-continued

| | % by weight |
|---|---|
| C20-40 alkyl stearate | 5.00 |
| Jojoba oil | 10.00 |
| Carnauba wax | 2.00 |
| Tocopheryl acetate | 0.75 |
| Water | 5.00 |
| Perfume, preservative, antioxidants etc. | q.s. |

EXAMPLE 15

Lipcare Gel

| | % by weight |
|---|---|
| Caprylic/capric triglycerides | 40.00 |
| Vaseline | 40.00 |
| Wool wax alcohol | 1.00 |
| Beeswax | 3.00 |
| Amiogum ® 23 (Starch Sodium Octenyl Succinate) | 0.25 |
| Polyisobutene | 5.00 |
| Jojoba oil | 8.00 |
| Tocopheryl acetate | 0.50 |
| Perfume, preservative, antioxidants etc. | q.s. |

EXAMPLE 16

Face Powder, Pressed

| | % by weight |
|---|---|
| Magnesium silicate | 25.00 |
| Magnesium stearate | 1.50 |
| Nylon-12 | 2.50 |
| Lauroyl lysine | 1.00 |
| Kaolin | 10.00 |
| Magnesium carbonate | 5.00 |
| Amiogum ® 23 (Starch Sodium Octenyl Succinate) | 3.50 |
| Mica | 5.00 |
| Iron oxide | 1.50 |
| Titanium dioxide | 2.50 |
| Isopropyl isostearate | 2.50 |
| Paraffin oil, subliquidum | 2.50 |
| Talc | ad 100.00 |
| Perfume, preservative, antioxidants etc. | q.s. |

EXAMPLE 17

Emulsion Make-Up

| | % by weight |
|---|---|
| Sorbitan monostearate | 1.50 |
| Sorbitan monooleate | 1.00 |
| Glyceryl monostearate | 1.00 |
| Paraffin oil, subliquidum | 7.00 |
| Octyldodecanol | 7.00 |
| Hydrogenated coconut fatty acid glycerides | 4.00 |
| Octyl methoxycinnamate | 2.00 |
| Butyl methoxydibenzoylmethane | 1.00 |
| Carbomer | 0.10 |
| Glycerol | 5.00 |
| 1,3-Butylene glycol | 2.00 |
| Tocopheryl acetate | 1.00 |

-continued

| | % by weight |
|---|---|
| Amiogum ® 23 (Starch Sodium Octenyl Succinate) | 2.50 |
| Magnesium silicate | 1.00 |
| Mica | 1.00 |
| Iron oxides | 1.00 |
| Titanium dioxide | 2.50 |
| Talc | 5.00 |
| Perfume, preservative, NaOH, dyes, antioxidants etc. | q.s. |
| Water | ad 100.00 |

What is claimed is:

1. A method for reducing the stickiness of a cosmetic or topical dermatological preparation, said method comprising incorporating in said cosmetic or topical dermatological preparation an amount of a compound which is sufficient to reduce the stickiness of said cosmetic or topical dermatological preparation, wherein said compound is a hydrophilic starch esterified with one or more n-octenylsuccinate radicals, which has the formula:

$$\text{starch-}X_n$$

wherein starch represents a hydrophilic starch;

X represents the radical:

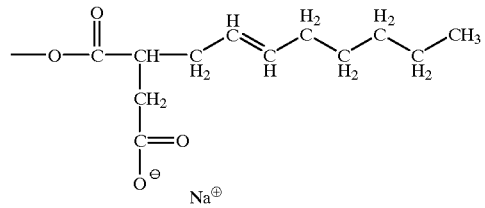

and n represents a number $\geq 1$.

2. The method according to claim 1, wherein said hydrophilic starch esterified with one or more n-octenylsuccinate radicals is incorporated in said cosmetic or topical dermatological preparation in an amount ranging from 0.01–25% by weight based on the total weight of the cosmetic or topical dermatological preparation.

3. The method according to claim 1, wherein said hydrophilic starch esterified with one or more n-octenylsuccinate radicals is incorporated in said cosmetic or topical dermatological preparation in an amount ranging from 0.1–10% by weight based on the total weight of the cosmetic or topical dermatological preparation.

4. The method according to claim 1, wherein said hydrophilic starch esterified with one or more n-octenylsuccinate radicals is incorporated in said cosmetic or topical dermatological preparation in an amount ranging from 0.2–5.0% by weight based on the total weight of the cosmetic or topical dermatological preparation.

5. A method for reducing the greasiness of a cosmetic or topical dermatological preparation, said method comprising incorporating in said cosmetic or topical dermatological preparation an amount of a compound which is sufficient to reduce the greasiness of said cosmetic or topical dermatological preparation, wherein said compound is a hydrophilic starch esterified with one or more n-octenylsuccinate radicals, which has the formula:

$$\text{starch-}X_n$$

wherein
   starch represents a hydrophilic starch;
   X represents the radical:

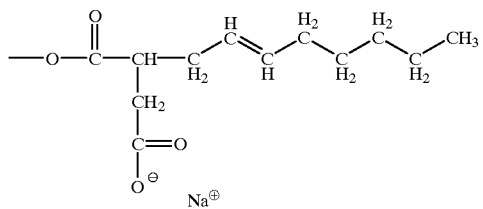

and
   n represents a number $\geq 1$.

6. The method according to claim 5, wherein said hydrophilic starch esterified with one or more n-octenylsuccinate radicals is incorporated in said cosmetic or topical dermatological preparation in an amount ranging from 0.01–25% by weight based on the total weight of the cosmetic or topical dermatological preparation.

7. The method according to claim 5, wherein said hydrophilic starch esterified with one or more n-octenylsuccinate radicals is incorporated in said cosmetic or topical dermatological preparation in an amount ranging from 0.1–10% by weight based on the total weight of the cosmetic or topical dermatological preparation.

8. The method according to claim 5, wherein said hydrophilic starch esterified with one or more n-octenylsuccinate radicals is incorporated in said cosmetic or topical dermatological preparation in an amount ranging from 0.2–5.0% by weight based on the total weight of the cosmetic or topical dermatological preparation.

* * * * *